United States Patent [19]
Shah et al.

[11] Patent Number: 5,869,489
[45] Date of Patent: Feb. 9, 1999

[54] TRYPTHOPHAN UREAS AS NEUROKINNIN ANTAGONISTS

[75] Inventors: Shrenik K. Shah, Metuchen; Hongbo Qi, Edison; Malcolm Maccoss, Freehold, all of N.J.

[73] Assignee: Merck & Co., Inc., Rahway, N.J.

[21] Appl. No.: 814,387

[22] Filed: Mar. 11, 1997

Related U.S. Application Data

[60] Provisional application No. 60/014,003 Mar. 25, 1996.
[51] Int. Cl.⁶ ............... A61K 31/495; C07D 401/12; C07D 403/12; C07D 471/10
[52] U.S. Cl. ............ 514/253; 514/259; 514/278; 514/323; 544/284; 544/373; 546/17; 546/201
[58] Field of Search ............... 546/17, 201; 544/284, 544/373; 514/253, 259, 278, 323

[56] References Cited

FOREIGN PATENT DOCUMENTS

94/01402  1/1994  WIPO .

OTHER PUBLICATIONS

Frossard et al, *Life Sciences*, 49, pp. 1941–1953, 1991.

*Primary Examiner*—Emily Bernhardt
*Attorney, Agent, or Firm*—Richard C. Billups; Curtis C. Panzer; David L. Rose

[57] ABSTRACT

Disclosed are Substituted azacycles of formula I

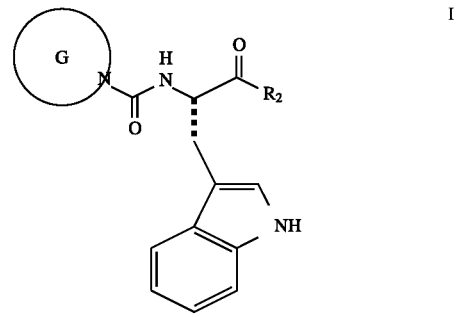

are tachykinin receptor antagonists useful in the treatment of inflammatory diseases, pain or migraine, and asthma. In particular compounds of formula I are shown to be neurokinin antagonists.

8 Claims, No Drawings

TRYPTHOPHAN UREAS AS NEUROKINNIN ANTAGONISTS

This application claims the benefit of U.S. provisional application No.60/014,003 filed Mar. 25, 1996.

BACKGROUND OF THE INVENTION

The invention disclosed herein is directed to certain substituted azacycles useful as tachykinin receptor antagonists. In particular, the compounds disclosed herein are neurokinin receptor antagonists.

The tachykinins, substance P (SP), neurokinin A (NKA) and neurokinin B (NKB), are structurally similar members of a family of neuropeptides. Each of these is an agonist of the receptor types, neurokinin-1 receptor (NK-1), neuorokinin-2 receptor (NK-2) and neuorokinin-3 receptor (NK-3), which are so defined according to their relative abilities to bind tachykinins with high affinity and to be activated by the natural agonists SP, NKA and NKB respectively.

The tachykinins are distinguished by a conserved carboxyl-terminal sequence Phe-X-Gly-Leu-Met-NH$_2$. More specifically, substance P is a pharmacologically-active neuropeptide that is produced in mammals and possesses a characteristic amino acid sequence:

Arg-Pro-Lys-Pro-Gln-Gln-Phe-Phe-Gly-Leu-Met-NH$_2$

Neurokinin A possesses the following amino acid sequence:

His-Lys-Thr-Asp-Ser-Phe-Val-Gly-Leu-Met-NH$_2$.

Neurokinin B possesses the following amino acid sequence:

Asp-Met-His-Asp-Phe-Phe-Val-Gly-Leu-Met-NH$_2$.

(Chang et al., Nature New Biol. 232, 86 (1971); D. F. Veber et al., U.S. Pat. No. 4,680,283).

The neurokinin receptors are widely distributed throughout the mammalian nervous system (especially brain and spinal ganglia), the circulatory system and peripheral tissues (especially the duodenum and jejunum) and are involved in regulating a number of diverse biological processes. This includes sensory perception of olfaction, vision, audition and pain, movement control, gastric motility, vasodilation, salivation, and micturition (B. Pernow, Pharmacol. Rev., 1983, 35, 85–141). The NK1 and NK2 receptor subtypes are implicated in synaptic transmission (Laneuville et al., Life Sci., 42: 1295–1305 (1988)).

Substance P acts as a vasodilator, a depressant, stimulates salivation and produces increased capillary permeability. It is also capable of producing both analgesia and hyperalgesia in animals, depending on dose and pain responsiveness of the animal (see R. C. A. Frederickson et al., Science, 199, 1359 (1978); P. Oehme et al., Science, 208, 305 (1980)) and plays a role in sensory transmission and pain perception (T. M. Jessell, Advan. Biochem. Psychopharmacol. 28, 189 (198 1)). In particular, substance P has been shown to be involved in the transmission of pain in migraine (see B. E. B. Sandberg et al., Journal of Medicinal Chemistry, 25, 1009 (1982)), and in arthritis (Levine et al. Science, (1984) 226, 547–549).

In the airways, it has been indicated that NK1 receptors are associated with microvascular leakage and mucus secretion, while NK2 receptors regulate smooth muscle contraction. Also, it has been shown that both substance P and neurokinin A are effective in inducing airway constriction and edema. Based on such findings, it is believed that substance P and neurokinin A may be involved in the pathogenesis of neurogenic inflammation, including allergic diseases such as asthma. (Frossard et al, Life Sci., 49, 1941–1953 (1991); Advenier, et al, Biochem. Biophys. Res. Comm., 184(3), 1418–1424 (1992)).

In experimental studies, sensory neuropeptides, especially tachykinins such as substance P and neurokinin A, can bring about many of the pathophysiological features of asthma. Neurokinin A is a very potent constrictor of human airways in vitro, and substance P causes mucus secretion in the airways. (Barnes P. J., Lancet, pp 242–44 (1986); Rogers D. R., Aursudkij B., Barnes P. J., Euro. J. Pharmacol, 174, 283–86 (1989)).

Inhalation of bradykinin causes bronchoconstriction in asthmatic patients but not in normal subjects. (Fuller R. W., Dixon C. M. S., Cuss F. M. C., Barnes P. J., Am Rev Respir Dis, 135, 176–80 (1987)). Since the bradykinin-induced bronchoconstriction is partly opposed by anticholinergic agents and since bradykinin is only a weak constrictor of human airways in vitro, it has been suggested that the bronchoconstrictor response is partly mediated by a neural reflex. Bradykinin stimulates vagal afferent C fibers and causes broncho-constriction in dogs. (Kaufman M. P., Coleridge H. M., Coleridge J. C. G., Baker D. G., J. Appl. Physio., 48, 511–17 (1980)). In guinea-pig airways, bradykinin causes a bronchoconstrictor response by way of cholinergic and sensory-nerve-mediated mechanisms. (Ichinoe M., Belvisi M. G., Barnes P. J., J. Pharmacol. Exp. Ther., 253, 594–99 (1990). Bradykinin-induced bronchoconstriction in human airways may therefore be due partly to tachykinin released from sensory nerve terminals via axon reflex mechanisms. Clinical trials have shown that a dual NK-1/NK-2 antagonist (such as FK-224) protects against bradykinin induced bronchocontriction in asthmatic patients. (Ichinoe, M. et al., Lancet, vol. 340, pp 1248–1251 (1992)).

The tachykinins have also been implicated in gastrointestinal (GI) disorders and diseases of the GI tract, such as inflammatory bowel disease, ulcerative colitis and Crohn's disease, etc. (see Mantyh et al., Neuroscience, 25 (3), 817–37 (1988) and D. Regoli in "Trends in Cluster Headache" Ed. F. Sicuteri et al., Elsevier Scientific Publishers, Amsterdam, 1987, pp. 85–95).

It is also hypothesized that there is a neurogenic mechanism for arthritis in which substance P may play a role (Kidd et al., "A Neurogenic Mechanism for Symmetric Arthritis" in The Lancet, 11 Nov. 1989 and Gronblad et al., "Neuropeptides in Synovium of Patients with Rheumatoid Arthritis and Osteoarthritis" in J. Rheumatol. (1988) 15(12) 1807–10). Therefore, substance P is believed to be involved in the inflammatory response in diseases such as rheumatoid arthritis and osteoarthritis (O'Byrne et al., in Arthritis and Rheumatism (1990) 33, 1023–8). Other disease areas where tachykinin antagonists are believed to be useful are allergic conditions (Hamelet et al, Can. J. Pharmacol. Physiol. (1988) 66, 1361–7), immunoregulation (Lotz et al., Science (1988) 241, 1218–21, Kimball et al., J. Immunol. (1988) 141 (10) 3564–9 and A. Perianin, et al., Biochem. Biophys. Res. Commun. 161, 520 (1989)) vasodilation, bronchospasm, reflex or neuronal control of the viscera (Mantyh et al., PNAS (1988) 85, 3235–9) and, possibly by arresting or slowing β-amyloid-mediated neurodegenerative changes (Yankner et al, Science, (1990) 250, 279–82) in senile dementia of the Alzheimer type, Alzheimer's disease and Downs Syndrome. Substance P may also play a role in demyelinating diseases such as multiple sclerosis and amyotrophic lateral sclerosis (J. Luber-Narod et al., poster presented at C.I.N.P. XVIIIth Congress, 28th Jun. –2nd Jul., 1992). Antagonists selective for the substance P and/or the neurokinin A receptor may be useful in the treatment of asthmatic disease (Frossard et al., Life Sci., 49, 1941–1953 (1991); Advenier, et al., Biochem. Biophys. Res. Comm., 184(3), 1418–1424 (1992)).

SUMMARY OF THE INVENTION

This invention is directed to compounds of formula I.

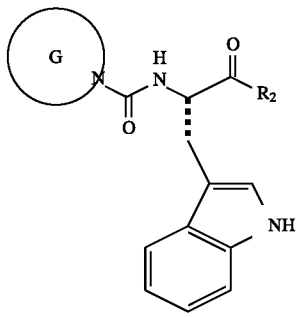

The invention is also concerned with pharmaceutical formulations with these novel compounds as active ingredients and the use of the novel compounds and their formulations in the treatment of certain disorders.

The compounds of this invention are tachykinin receptor antagonists and are useful in the treatment of inflammatory diseases, pain or migraine and asthma.

DETAILED DESCRIPTION OF THE INVENTION

This invention is directed to compounds of formula I.

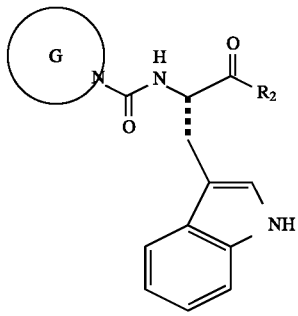

or a pharmaceutically acceptable salt thereof, wherein

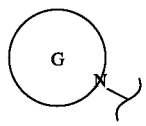

is selected from the group consisting of

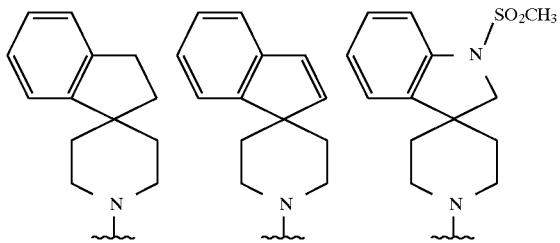

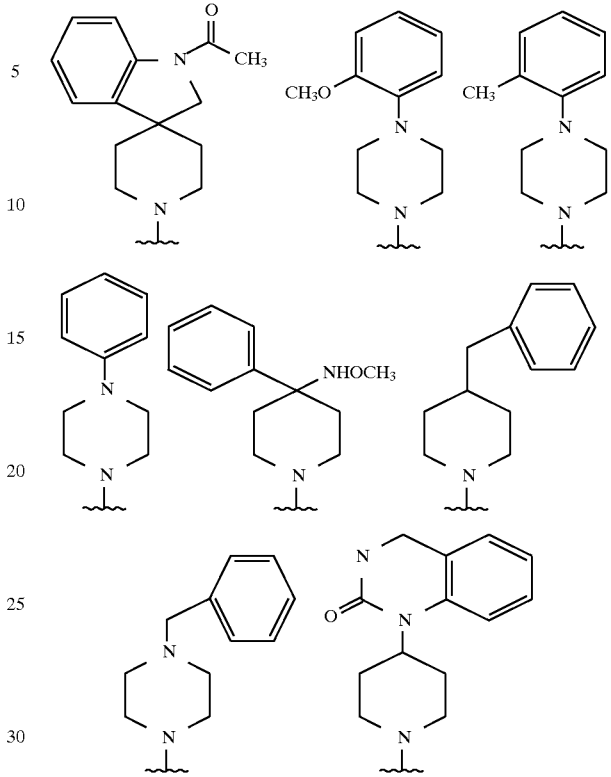

$R_2$ is
(a) —OCH$_2$phenyl, wherein the phenyl is optionally mono di or trisubstituted phenyl wherein the substitutents are independently halo, methyl or CF$_3$;
(b) —N(R$_3$)C$_{1-4}$alkylphenyl, wherein the C$_{1-4}$alkyl may be linear or branched, the phenyl is optionally mono di or trisubstituted and wherein the substitutents are independently halo, methyl, methoxy or CF$_3$ and n is 1, or 2;
R$_3$ is H, methyl or ethyl.

Within this embodiment there is a genus of compounds wherein
R$_2$ is
(a) —OCH$_2$phenyl, wherein the phenyl is optionally mono di or trisubstituted phenyl wherein the substitutents are independently halo, methyl, methoxy or CF$_3$;
(b) —NHCH$_2$phenyl, wherein the phenyl is optionally mono di or trisubstituted phenyl wherein the substitutents are independently halo, methyl, methoxy or CF$_3$;
(c) —N(CH$_3$)CH$_2$phenyl, wherein the phenyl is optionally mono di or trisubstituted phenyl wherein the substitutents are independently halo, methyl, methoxy or CF$_3$;
(d) —N(CH$_3$)CH(CH$_3$)phenyl, wherein the phenyl is optionally mono di or trisubstituted phenyl wherein the substitutents are independently halo, methyl, methoxy or CF$_3$; and
(f) —N(CH$_3$)CH(CH$_2$CH$_3$)phenyl, wherein the phenyl is optionally mono di or trisubstituted phenyl wherein the substitutents are independently halo, methyl, methoxy or CF$_3$.

Within this genus there is a class of compounds wherein

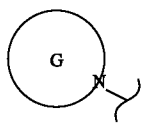

is selected from the group consisting of

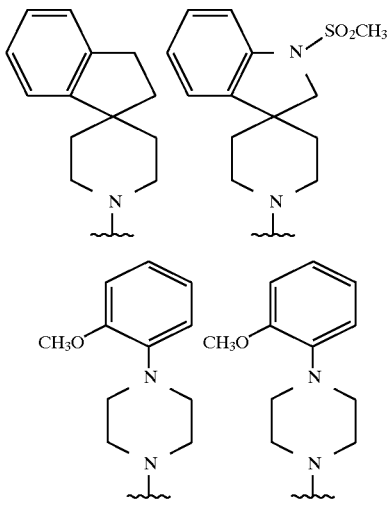

As appreciated by those of skill in the art, halo as used wherein are intended to include chloro, fluoro, bromo and iodo.

Exemplifying the invention are the compounds of the examples including the group consisting of (a) N-Benzyl-N-methyl-2-(S)-((spiro-1H-indene-,4'-piperidino)-carbonyl-amino)-3-(3-indolyl)propionamide, (b) N-Benzyl-2-(S)-((1-methanesulfonyl-spiroindoline-3,4'-piperidino)-carbonyl-amino)-3-(3-indolyl) propionamide, (c) 3,5-Bistrifluoromethylbenzyl 2-(S)-((spiro-1H-indene-1,4'-piperidino)-carbonyl-amino)-3-(3-indolyl)propionate, (d) N-Benzyl-N-methyl-2-(S)-((spiroindane- 1,4'-piperidino)-carbonyl-amino)-3-(3-indolyl)propionamide, (e) N-Benzyl-N-methyl-2-(S)-((1-methanesulfonyl-spiroindoline-3,4'-piperidino)-carbonyl-amino)-3-(3-indolyl)propionamide, (f) N-Benzyl-N-methyl-2-(S)-((1-acetylspiroindoline-3,4'-piperidino)-carbonyl-amino)-3-(3-indolyl)propionamide, (g) N-Benzyl-N-methyl-2-(S)-(4-phenylpiperidino)-carbonyl-amino)-3-(3-indolyl)propionamide, (h) N-Benzyl-N-methyl-2-(S)-((4-benzylpiperidino)-carbonyl-amino)-3-(3-indolyl)propionamide, (i) N-Benzyl-N-methyl-2-(S)-(((4-phenyl-4-acetylamino)piperidino)-carbonyl-amino)-3-(3-indolyl)propionamide, (j) N-Benzyl-N-methyl-2-(S)-((4-benzylpiperazino)-carbonyl-amino)-3-(3-indolyl)propionamide, (k) N-Benzyl-N-methyl-2-(S)-(4-(2-oxo-1,2,3,4-tetrahydroquinazolin-1-yl)piperidino)-carbonyl-amino)-3-(3-indolyl)propionamide, (l) N-Benzyl-N-methyl-2-(S)-((4-(2-methoxyphenyl) piperazino)-carbonyl-amino)-3-(3-indolyl)propionamide, (m) N-Benzyl-N-methyl-2-(S)-((4-(2-methylphenyl) piperazino)-carbonyl-amino)-3-(3-indolyl)propionamide, (n) N-Phenyl-2-(S)-((spiroindane-1,4'-piperidino)-carbonyl-amino)-3-(3-indolyl)propionamide, (o) N-Benzyl-2-(S)-((spiroindane-1,4'-piperidino)-carbonyl-amino)-3-(3-indolyl)propionamide, (p) N-(2-Methylbenzyl)-2-(S)-((spiroindane-1,4'-piperidino)-carbonyl-amino)-3-(3-indolyl)propionamide, (o) N-(3-Methylbenzyl)-2-(S)-((spiroindane-1,4'-piperidino)-carbonyl-amino)-3-(3-indolyl)propionamide, (p) N-(4-Methylbenzyl)-2-(S)-((spiroindane-1,4'-piperidino)-carbonyl-amino)-3-(3-indolyl)propionamide, (q) N-(2-Phenylethyl)-2-(S)-((spiroindane-1,4'-piperidino)-carbonyl-amino)-3-(3-indolyl)propionamide, (r) N-Benzyl-N-ethyl-2-(S)-((spiroindane-1,4'-piperidino)-carbonyl-amino)- 3-(3-indolyl)propionamide, (s) N-(1(S)-Phenylethyl)-2(S)-((spiroindane-1,4'-piperidino)-carbonyl-amino)-3-(3-indolyl)propionamide, (t) N-(1(R)-Phenylethyl)-2(S)-((spiroindane-1,4'-piperidino)-carbonyl-amino)-3-(3-indolyl)propionamide, (u) N-(1(S)-Phenylpropyl)-N-methyl-2(S)-((spiroindane-1,4'-piperidino)-carbonyl-amino)-3-(3-indolyl)propionamide, (v) N-(1(R)-Phenylpropyl)-N-methyl-2(S)-((spiroindane-1,4'-piperidino)-carbonyl-amino)-3-(3-indolyl)propionamide, (w) N-(3-Methylphenyl)methyl-N-methyl-2-(S)-((1-methanesulfonyl-spiroindoline-3,4'-piperidino)-carbonyl-amino)-3-(3-indolyl)propionamide, (x) N-(3-Trifluoromethylphenyl)methyl-N-methyl-2-(S)-((1-methanesulfonyl-spiroindoline-3,4'-piperidino)-carbonyl-amino)-3-(3-indolyl)propionamide, (y) N-(3,5-Dichlorophenyl)methyl-N-methyl-2-(S)-((1-methanesulfonyl-spiroindoline-3,4'-piperidino)-carbonyl-amino)-3-(3-indolyl)propionamide, (ab) N-(3,5-Dimethylphenyl)methyl-N-methyl-2-(S)-((1-methanesulfonyl-spiroindoline-3,4'-piperidino)-carbonyl-amino)-3-(3-indolyl)propionamide, (ac) N-((3-Chloro-5-methyl)phenyl)methyl-N-methyl-2-(S)-((1-methanesulfonyl-spiroindoline-3,4'-piperidino)-carbonyl-amino)-3-(3-indolyl)propionamide, (ad) N-(1(S)-phenyl)ethyl-N-methyl-2-(S)-((1-methanesulfonyl-spiroindoline-3,4'-piperidino)-carbonyl-amino)-3-(3-indolyl)propionamide, (ae) N-Benzyl-N-methyl-2-(R)-((spiro-1H-indene-1,4'-piperidino)-carbonyl-amino)-3-(3-indolyl)propionamide (af) N-Benzyl-N-methyl-2-(R)-((1-methanesulfonyl-spiroindoline-3,4'-piperidino)-carbonyl-amino)-3-(3-indolyl)propionamide, (ag) N-Benzyl-N-methyl-2-(R)-(4-phenylpiperidino)-carbonyl-amino)-3-(3-indolyl)propionamide, (ah) N-Benzyl-N-methyl-2-(S)-((1-methanesulfonyl-spiroindoline-3,4'-piperidino)-carbonyl-amino)-4-phenylbutyramide, (ai) N-Benzyl-N-methyl-2-(S)-((1-methanesulfonyl-spiroindoline-1,4'-piperidino)-carbonyl-amino)-3-benzyloxypropionamide, (aj) N-Benzyl-N-methyl-2-(S)-((spiroindine-1,4'-piperidino)-carbonyl-amino)-3-phenylpropionamide, and (ak) N-Benzyl-N-methyl-2-(S)-((spiroindine-1,4'-piperidino)-carbonyl-amino)-2-phenylacetamide.

In an alternative embodiment the above compounds may be co-administered with a β2-agonist such as Bambuterol, U.S. Pat. No. 4,419,364 issued to Draco on Dec. 6, 1983; Bitolterol mesylate, U.S. Pat. No. 4,138,581 issued to Sterling Feb. 6, 1979; Carbuterol, U.S. Pat. No. 3,763,232 issued to SmithKline Oct. 2, 1973; Clenbuterol, U.S. Pat. No. 3,536,712 issued to Boehringer Ingelheim Oct. 27, 1970; Dopexamine, U.S. Pat. No. 4,645,768 issued to Fisons Feb. 24, 1987; Formoterol, U.S. Pat. No. 3,994,974 issued to Yamanouchi Nov. 30, 1976; Mabuterol, U.S. Pat. No. 4,119,710 issued to Boehringer Ingelheim Oct. 10, 1978; Pirbuterol hydrochloride U.S. Pat. No. 3,700,681 issued to Pfizer Oct. 24, 1972; Procaterol hydrochloride U.S. Pat. No.

4,026,897 issued to Otsuka May 31, 1977; Ritodrine hydrochloride U.S. Pat. No. 3,410,944 issued to North American Philips Nov. 12, 1968; Brosaterol, U.S. Pat. No. 4,276,299 issued to Zambon Jun. 30, 1981 and U.S. Pat. No. 4,520,200 issued to Zambon May 28, 1985; Cimaterol, U.S. Pat. No. 4,407,819 issued to American Cyanamid Oct. 4, 1983; Docarpamine, U.S. Pat. No. 4,228,183 issued to Tanabe Oct. 14, 1980; Salmeterol, U.S. Pat. No. 4,992,474 issued to Glaxo Feb. 21, 1991 and U.S. Pat. No. 5,091,422 issued to Glaxo Feb. 25, 1992.

The compounds of formula I are particularly useful in the treatment of diseases or conditions that are advantageously treated by concomitant antagonism of both NK1 and NK2 receptors or NK1, NK2 and NK3 receptors. These diseases include neuropathy, such as diabetic or peripheral neuropathy and chemotherapy-induced neuropathy; asthma; osteoarthritis; rheumatoid arthritis; and migraine.

In a second alternative embodiment the compounds of formula I may be co-administered with another NK1 or NK2 antagonist such as those described in Appln No. DO-139125, filed 8 Jun. 1978, Pub. 12 Dec. 1979; application No. EP-82568, filed 22 Dec. 1981, Pub. 29 Jun. 1983; application No. EP-490379, filed 13 Dec. 1990, Pub. 17 Jun. 1992; application No. EP-353732, filed 5 Aug. 1988, Pub. 7 Feb. 1990; application No. EP-161007, filed 13 Jan. 1984, Pub. 13 Nov. 1985; application No. EP-385-43, filed 28 Feb. 1989, Pub. 5 Sep. 1990; application No. WO8301251, filed 9 Oct. 1981, Pub. 14 Apr. 1983; application No. BE-894602, filed 9 Oct. 1981, Pub. 31 Jan. 1983; application No. DE3205991, filed 19 Feb. 1982, Pub. 1 Sep. 1983; application No. EP-327009, filed 2 Feb. 1988, Pub. 9 Aug. 1989; application No. EP-336230, filed 5 Apr. 1988, Pub. 11 Oct. 1989; application No. 394989, filed 28 Apr. 1989, Pub. 31 Oct. 1990; application No. AU9068010, filed 22 Dec. 1989, Pub. 27 Jun. 1991; application No. EP-482539, filed 24 Oct. 1990, Pub. 29 Apr. 1992; application No. EP-443132, filed 10 Dec. 1990, Pub. 28 Aug. 1991; application No. EP-498069, filed 21 Dec. 1990, Pub. 12 Aug. 1992; application No. WO9222569, filed 19 Jun. 1991, Pub. 23 Dec. 1992; application No. JO 4297492, filed 24 Oct. 1991, Pub. 21 Oct. 1992; application No. U.S. Pat. No. 4997853, filed 2 Dec. 1988, Pub. 5 Mar. 1991; application No. EP-272929, filed 24 Dec. 1986, Pub. 29 Jun. 1988; application No. EP-360390, filed 25Jul. 1988, Pub. 28Mar. 1990; application No. U.S. Pat. No. 3862114, filed 22 Nov. 1971, Pub. 21 Jan. 1975; application No. EP-219258, filed 30 Sep. 1985, Pub. 22Apr. 1987, application No. U.S. Pat. No. 4742156, filed 30 Sep. 1985, Pub. 3 May 1988; application No. EP-401177, filed 29 May 1989, Pub. 5 Dec. 1990; application No. WO9202546, filed 3 Aug. 1990, Pub. 20 Feb. 1992; application No. EP176436, filed 26 Sep. 1984, Pub. 2 Apr. 1986; application No. U.S. Pat. No. Pat. No. 4680283, filed 26 Sep. 1984, Pub. 14 Jul. 1987; application No. WO9220661, filed 22 May 1991, Pub. 26 Nov. 1992; application No. EP-520555, filed 24 Jun. 1991, Pub. 30 Dec. 1992; application No. EP-347802, filed 20 Jun. 1988, Pub. 27 Dec.1989; application No. EP-412542, filed 10 Aug. 1989, Pub. 13 Feb. 1991; application No. WO9005729, filed 23 Nov. 1988, Pub. 31 May 1990; application No. WO9005525, filed 23 Nov. 1988, Pub. 31 May 1990; application No. EP-436334, filed 4 Jan. 1990, Pub. 10 Jul. 1991; application No. WO9118878, filed 31 May 1990, Pub. 12 Dec. 1991; application No. WO9118899, filed 1 Jun. 1990, Pub. 12 Dec. 1991; application No. WO9201688, filed 23 Jul. 1990, Pub. 6 Feb. 1992; application No. WO9206079, filed 28 Sep. 1990, Pub. 16 Apr. 1992; Appln No. WO9212152, filed 3 Jan. 1991, Pub. 23 Jul. 1992; application No. WO9212151, filed 10 Jan. 1991, Pub. 23 Jul. 1992; WO09215585, filed 1 Mar. 1991, Pub. 29 Apr. 1992; application No. WO022-676, filed 22 May 1991, Pub. 26 Nov. 1992; application No. WO9221677, filed 31 May 1991, Pub. 10 Dec. 1992; application No. WO9300331, filed 20 Jun. 1991, Pub. 7 Jun. 1993; application No. WO9300330, filed 21 Jun. 1991, Pub. 7 Jan. 1993; application No. WO9109844, filed 11 Jul. 1991, Pub. 11 Jul. 1991; application No. EP-429366, filed 23 Nov. 1989, Pub. 29 May 1991; application No. EP-430771, filed 23 Nov. 89, Pub. 5 Jun. 1991; application No. EP-514274, filed 17 May 1991, Pub. 19 Nov. 1992; application No. EP-514276, filed 17 May 1991, Pub. 19 Nov. 1992; Appln No. EP-514275, filed 17 May 1991, Pub. 19 Nov. 1992; application No. EP-514273, filed 17 May 1991, Pub. 19 Nov. 1992; application No. EP-428434, filed 6 Nov. 1989, Pub. 22 May 1991; application No. EP-474561, filed 9 May 1990, Pub. 11 Mar. 1992; application No. EP-512901, filed 3 May 1991, Pub. 19 Nov. 1992; application No. EP-512902, filed 3 May 1991, Pub. 11Nov. 1992; application No. EP-515240, filed 3 May 1991, Pub. 25 Nov. 1992; application No. U.S. Pat. No. 4472305, filed 17 May 1983, Pub. 18 Sep. 1984; application No. U.S. Pat. No. 4839465, filed 20 Jan. 1987, Pub. 13 Jun. 1989; application No. EP-101929, filed 28 Jul. 1982, Pub. 7Mar. 1984; application No. WO9102745, filed 16 Aug. 1989, Pub. 7 Mar. 1991; application No. U.S. Pat. No. 3912711, filed 3 Jul. 1972, Pub. 14 Oct. 1975; application No. U.S. Pat. No. 4059693, filed 11 Jun. 1976, Pub. 22 Nov. 77; application No. U.S. Pat. No. 4481139, filed 13 Apr. 1983, Pub. 6 Nov. 1984; application No. U.S. Pat. No. 7358073, filed 24 Oct. 1988, Pub. 19 Dec. 1989; application No. U.S. Pat. No. 7261627, filed 24 Oct. 1988, Pub. 7 Mar. 1989, which are hereby incorporated by reference.

The compounds of formula I are useful in the prevention and treatment of a wide variety of clinical conditions (as detailed in this specification) which are characterized by overstimulation of the tachykinin receptors, in particular NK 1, NK 2 and NK 3.

These conditions may include disorders of the central nervous system such as anxiety, depression, psychosis and schizophrenia; neurodegenerative disorders such as AIDS related dementia, senile dementia of the Alzheimer type, Alzheimer's disease and Down's syndrome; demyelinating diseases such as multiple sclerosis and amyotrophic lateral sclerosis and other neuropathological disorders such as diabetic or peripheral neuropathy, AIDS related neuropathy, chemotherapy-induced neuropathy, and neuralgia; respiratory diseases such as chronic obstructive airways disease, bronchopneumonia, bronchospasm and asthma; inflammatory diseases such as inflammatory bowel disease, psoriasis, fibrositis, osteoarthritis and rheumatoid arthritis; allergies such as eczema and rhinitis; hypersensitivity disorders such as poison ivy; ophthalmic diseases such as conjunctivitis, vernal conjunctivitis, and the like; cutaneous diseases such as contact dermatitis, atopic dermatitis, urticaria, and other eczematoid dermatitis; addiction disorders such as alcholism; stress related somatic disorders; reflex sympathetic dystrophy such as shoulder/hand syndrome; dysthymic disorders; adverse immunological reactions such as rejection of transplanted tissues and disorders related to immune enhancement or suppression such as systemic lupus erythematosis; gastrointestinal (GI) disorders and diseases of the GI tract such as disorders associated with the neuronal control of viscera such as ulcerative colitis, Crohn's disease and incontinence; disorders of bladder function; fibrosing and collagen diseases such as scleroderma and eosinophilic fascioliasis; disorders of blood flow caused by vasodilation and vasospastic diseases such as angina, migraine and Reynaud's disease; and pain or nociception, for example, that is attributable to or associated with any of the foregoing conditions especially the transmission of pain in migraine. Hence, these compounds are readily adapted to therapeutic use for the treatment of physiological disorders associated with the overstimulation of the tachykinin receptors, in particular NK 1, NK 2 and NK 3.

The compounds of the present invention are particularly useful in the treatment of pain or nociception and/or inflammation and disorders associated therewith such as, for example: neuropathy, such as diabetic or peripheral neuropathy and chemotherapy-induced neuropathy; asthma; osteoarthritis; rheumatoid arthritis; and migraine.

For the treatment of any of these diseases compounds of Formula I may be administered orally, topically, parenterally, ICV, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intracisternal injection or infusion techniques. In addition to the treatment of warm-blooded animals such as mice, rats, horses, cattle, sheep, dogs, cats, etc., the compounds of the invention are effective in the treatment of humans.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl- pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of formula I may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compounds of Formula I are employed. (For purposes of this application, topical application shall include mouth washes and gargles.)

In the treatment of a condition associated with an excess of tachykinins, an appropriate dosage level will generally be about 0.001 to 50 mg per kg patient body weight per day which can be administered in single or multiple doses. Preferably, the dosage level will be about 0.01 to about 25 mg/kg per day; more preferably about 0.05 to about 10 mg/kg per day. A suitable dosage level may be about 0.001 to 25 mg/kg per day, about 0.005 to 10 mg/kg per day, or about 0.005 to 5 mg/kg per day. Within this range the dosage may be 0.005 to 0.05, 0.05 to 0.5 or 0.5 to 5.0 mg/kg per day. The compounds may be administered on a regimen of 1 to 4 times per day, preferably once or twice per day.

TACHYKININ ANTAGONISM ASSAY

The compounds of this invention are useful for antagonizing tachykinins, in particular substance P and neurokinin A in the treatment of gastrointestinal disorders, central nervous system disorders, inflammatory diseases, pain or migraine and asthma in a mammal in need of such treatment. This activity can be demonstrated by the following assay.

A. Receptor Expression in COS

To express the cloned human neurokinin-1 receptor (NK 1R) transiently in COS, the cDNA for the human NK 1R was cloned into the expression vector pCDM9 which was derived from pCDM 8 (INVITROGEN) by inserting the ampicillin resistance gene (nucleotide 1973 to 2964 from BLUESCRIPT SK+) into the Sac II site. Transfection of 20 μg of the plasmid DNA into 10 million COS cells was achieved by electroporation in 800 μl of transfection buffer (135 mM NaCl, 1.2 mM $CaCl_2$, 1.2 mM $MgCl_2$, 2.4 mM $K_2HPO_4$, 0.6 mM $KH_2PO_4$, 10 mM glucose, 10 mM HEPES pH 7.4) at 260 V and 950 uF using the IBI GENEZAPPER (IBI, New Haven, Conn.). The cells were incubated in 10% fetal calf serum, 2 mM glutamine, 100 U/ml penicillin-streptomycin, and 90% DMEM media (GIBCO, Grand Island, N.Y.) in 5% $CO_2$ at 37° C. for three days before the binding assay. Similar methods were used to express the NK2 receptor.

B. Stable Expression in CHO

To establish a stable cell line expressing the cloned human NK1R, the cDNA was subcloned into the vector pRcCMV (INVITROGEN). Transfection of 20 μg of the plasmid DNA into CHO cells was achieved by electroporation in 800 μl of transfection buffer suplemented with 0.625 mg/ml Herring sperm DNA at 300 V and 950 uF using the IBI GENEZAPPER (IBI). The transfected cells were incubated in CHO media (10% fetal calf serum, 100 U/ml pennicilin-streptomycin, 2 mM glutamine, 1/500 hypoxanthine-thymidine (ATCC), 90% IMDM media (JRH BIOSCIENCES, Lenexa, Kans.), 0.7 mg/ml G418 (GIBCO)) in 5% $CO_2$ at 37° C. until colonies were visible. Each colony was separated and propagated. The cell clone with the highest number of human NK1R was selected for subsequent applications such as drug screening. Similar methods were used to express the human NK2 receptor.

C. Assay Protocol using COS or CHO The binding assay of human NK1R expressed in either COS or CHO cells is based on the use of $^{125}$I-substance P ($^{125}$I-SP, from DU PONT, Boston, Mass.) as a radioactively labeled ligand which competes with unlabeled substance P or any other ligand for binding to the human NK1R. Monolayer cell cultures of COS or CHO were dissociated by the non-enzymatic solution (SPECIALTY MEDIA, Lavallette, N.J.) and resuspended in appropriate volume of the binding buffer (50 mM Tris pH 7.5, 5 mM $MnCl_2$, 150 mM NaCl, 0.04 mg/ml bacitracin, 0.004 mg/ml leupeptin, 0.02 mg/ml BSA, 0.01 mM phosphoramidon) such that 200 μl of the cell suspension would give rise to about 10,000 cpm of specific $^{125}$I-SP binding (approximately 50,000 to 200,000 cells). In the binding assay, 500 μl of cells were added to a tube containing 20 μl of 1.5 to 0.25 nM of $^{125}$I-SP and 5 μl of unlabeled substance P or any other test compound in DMSO. The tubes were incubated at 4° C. or at room temperature for 1 hour with gentle shaking. The bound radioactivity was separated from unbound radioactivity by GF/C filter (BRANDEL, Gaithersburg, Md.) which was pre-wetted with 0.1% polyethylenimine. The filter was washed with 3 ml of wash buffer (50 mM Tris pH 7.5, 5 mM $MnCl_2$, 150 mM NaCl) three times and its radioactivity was determined by gamma counter. A similar assay was used for NK2 except $^{125}$I-NKA was used as the ligand.

The activation of phospholipase C by NK1R may also be measured in CHO cells expressing the human NK1R by determining the accumulation of inositol monophosphate which is a degradation product of $IP_3$. CHO cells are seeded in 12-well plate at 250,000 cells per well. After incubating in CHO media for 4 days, cells are loaded with 0.025 uCi/ml of $^3$H-myoinositol by overnight incubation. The extracellular radioactivity is removed by washing with phosphate buffered saline. LiCl is added to the well at final concentration of 0.1 mM with or without the test compound, and incubation is continued at 37° C. for 15 min. Substance P is added to the well at final concentration of 0.3 nM to activate the human NK1R. After 30 min of incubation at 37° C., the media is removed and 0.1N HCl is added. Each well is sonicated at 4° C. and extracted with $CHCl_3$/methanol (1:1). The aqueous phase is applied to a 1 ml Dowex AG1×8 ion exchange column. The column is washed with 0.1N formic acid followed by 0.025M ammonium formate-0.1N formic acid. The inositol monophosphate is eluted with 0.2M ammonium formate-0.1N formic acid and quantitated by beta counter. Similar methods were used to assess antagonism at the NK2 receptor, except NKA was used as the stimulating agonist.

The compounds of of Formula I as Exemplified in the EXAMPLES below have been found to displace radioactive ligand for the NK-1 receptor at a concentration range of 0.01 nM to 1.0 μM, for the NK-2 receptor, 0.01 nM to 5 μM, and for the NK-3 receptor, 1.0 nM to 10 μM.

Several methods for preparing the compounds of this invention are illustrated in the following Schemes and Examples. As this invention relates to tryptophan derivatives with substitution on the amine as well as the acid moieties two complementary approaches are used.

In one approach illustrated in Scheme 1 the acid group of Boc-tryptophan is first activated by reacting with hydroxybenzotriazole (HOBt) and a carbodiimide such as dicyclohexylcarbodiimide (DCC) or 1-(3-dimethylaminopropyl)-3-ethylcarbodiimide hydrochloride (EDC) in presence of a base such as N-methylmorpholine (NMM) and the intermediate is reacted with an appropriate amine or alcohol to form an amide or an ester. Other coupling protocols such as N-hydroxysuccinimide, DCC, BOP-Cl, isobutylchloroformate or carbonyldiimidazole may also be used in this step. Next the Boc protecting group is removed by treatment with an acid such as trifluoroacetic acid (TFA), formic acid or HCl-EtOAc. The free amine (or its salt) is next reacted with carbonyldiimidazole optionally in presence of a base such as triethylamine and the resulting acyl-imidazole intermediate is reacted with an azacycle to obtain the desired urea product. These required azacycles are either commercially available or are prepared by the methods described in the literature such as Parham, W. E. et al, Journal of Organic Chemistry, 1976, 41, 2628–2633, Ong, H. H. et al, Journal of Medicinal Chemistry, 1983, 26, 981–986, Evans, B. E. et al, U.S. Pat. No. 5,091,387, and Nargund, R. et al, WO94/19367, published Sep. 1, 1994, WO94/13696, published Jun. 23, 1994, 1993), EP 93/309,867,5 hereby incorporated by reference. None of the compounds in this references are claimed to be neurokinin antagonists. Alteranatively the amine obtained after removal of the protecting group is reacted with phosgene or triphosgene to generate a carbamoyl chloride which is then reacted with the azacycle. One can also react the azacycle with carbonyl diimidazole, phosgene or triphosgene first and then the resulting acylimidazole or carbamoyl chloride is reacted with the tryptophan derived amine to prepare the urea.

SCHEME 1

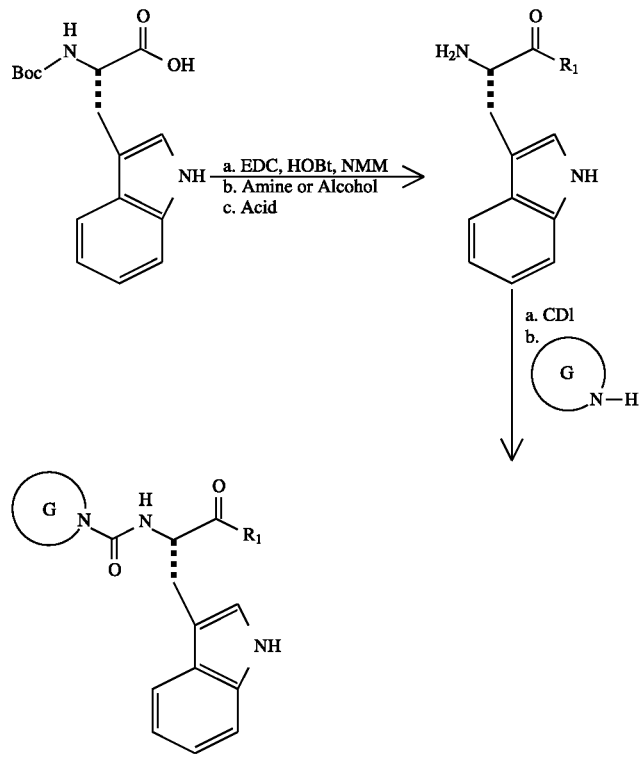

In the second method illustrated in Scheme 2 and described in example 2, the order of derivatization is changed. In this case one starts with a tryptophan where the acid moiety is protected and the amine is first transformed to the desired urea by one of the methods discussed 10 above. The benzyl ester protecting group is now removed by hydrogenation and the acid formed is coupled with the desired amine or an alcohol by the usual methods.

SCHEME 2

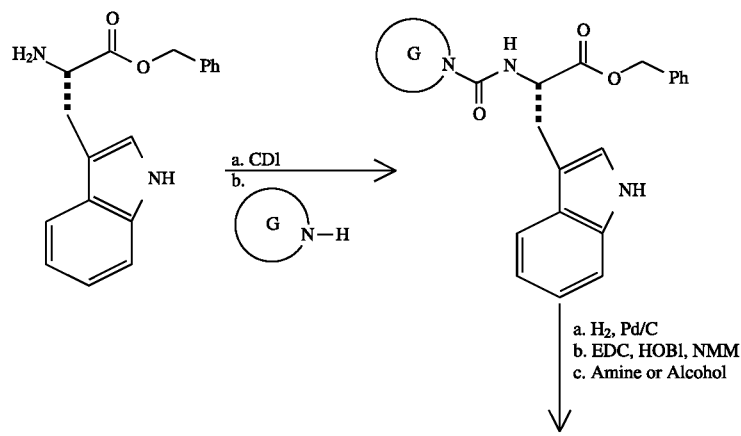

-continued
SCHEME 2

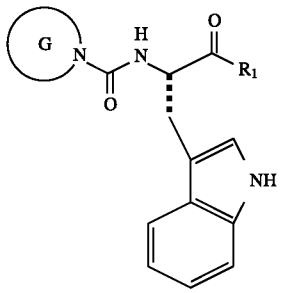

Although the methods described here uses a Boc protecting group for the amine moiety and a benzyl ester as a protecting group for the acid function of tryptophan, it is understood that other amine protecting groups such as Cbz, Fmoc, Alloc and acid protecting groups like t-butyl, allyl trichloroethyl ester may also be employed. The choice of the protecting group will be based on the individual compound of interest.

EXAMPLE 1

N-Benzyl-N-methyl-2-(S)-((spiro-1H-indene-1,4'-piperidino)-carbonyl-amino)-3-(3-indolyl) propionamide Step A: N-Methyl-N-benzyl-2-(S)-t-butyloxycarbonylamino-3-(3-indolyl)propionamide To a suspension of 1.967 g (6.46 mmol) of t-butylcarbonyloxy-L-tryptophan in 25 mL of $CH_2Cl_2$ N-methylmorpholine (1 mL, 9.69 mmol) was added. To the resulting clear solution 1.05 g (7.75 mol) of hydroxybenztriazole and 1.54 g (7.76 mmol) of 1-(3-dimethylaminopropyl)-3-ethylcarbodiimide hydrochloride (EDC) were added. After stirring for 15 min the reaction was treated with 0.87 mL (6.79 mmol) of N-benzyl-methylamine and the solution was stirred overnight. The reaction mixture was quenched with water and extracted with $CH_2Cl_2$. Each $CH_2Cl_2$ layer was washed with 1.2N HCl, saturated $NaHCO_3$, brine and dried. The combined filtrate was concentrated to yield 2.56 g of the title compound which was used in the next step without purification.

$^1$H NMR ($CDCl_3$, ppm ranges are listed because amide rotomers were present) δ1.39 and 1.43 (2s, 9H), 2.52 and 2.73 (2s, 3H), 3.17 (d, 2H), 3.9–4.4 (m, 2H), 4.98 (q, 1H), 5.42 and 5.47 (2d, 1H), 6.85–8.1 (m, 11H).

Step B: N-Methyl-N-benzyl-2-(S)-amino-3-(3-indolyl) propionamide

Cold trifluoroacetic acid (TFA, 4 mL) and 0.36 mL of anisole (3.28 mmol) were added to 1.215 g (2.98 mmol) of N-methyl-N-benzyl-2-(S)-t-butyloxycarbonylamino-3-(3-indolyl)propionamide and the resulting solution was stirred at 0° C. for 15 min. The ice bath was removed and the solution was allowed to warm to room temperature. After 30 min the reaction mixture was concentrated and the residue was partitioned between saturated $NaHCO_3$ and $CH_2Cl_2$. The organic layer was washed with brine, dried and concentrated leaving 1.044 g of the title compound which was used in the next step without purification.

$^1$H NMR ($CDCl_3$, ppm ranges are listed because amide rotomers were present) δ2.72 and 2.87 (2s, 3H), 2.9–3.2 (m, 2H), 3.95–3.6 (m, 3H), 6.85–7.6 (m, 10H), 8.17 (br s, 1H).

Step C: N-Methyl-N-benzyl-2-(S)-((spiro-1H-indene-4,1'-piperidino)-carbonyl-amino)-3-(3-indolyl)propionamide (L-743,516)

To a solution of 96 mg (0.325 mmol) of N-methyl-N-benzyl-2-(S)-amino-3-(3-indolyl)propionamide in 1.5 mL of THF, 58 mg (0.357 mmol) of carbonyldiimidazole (CDI) was added. After 10 min 76 mg (0.341 mmol) of spiro-1H-indene-1,4'-piperidine hydrochloride and 54 uL (0.39 mmol) of triethylamine ($Et_3N$) were added. A TLC of the reaction mixture after 4 h showed that the reaction was incomplete so another 30 mg (mmol) of spiro-1H-indene-1,4'-piperidine hydrochloride was added and the solution was stirred for 1 h. The reaction was quenched by adding water and extracted with EtOAc. The EtOAc layer was washed with brine, dried and the filtrate was concentrated. The residue was purified by chromatography using 50–60% EtOAc-Hexane to isolate 0.205 g of the title compound.

$^1$H NMR ($CDCl_3$, ppm ranges are listed because amide rotomers were present) δ1.3 (m, 2H), 1.95 (m, 2H), 2.61 and 2.8 (2s, 3H), 3.0–3.3 (m, 4H), 3.9–4.6 (m, 4H), 5.28 (m, 1H), 5.49 and 5.58 (2d, 1H), 6.7–7 (m, 15H), 7.5 and 7.71 (2d, 1H), 8.13 and 8.23 (2br s, 1H).

EXAMPLE 2

N-Benzyl-2-(S)-((1-methanesulfonyl-spiroindoline-3,4'-piperidino)-carbonyl-amino)-3-(3-indolyl) propionamide Step A: Benzyl 2-(S)-((1-methanesulfonyl-spiroindoline-3,4'-piperidino)-carbonyl-amino)-3-(3-indolyl)propionate(L-744,393)

To a solution of 0.331 g (1 mmol) of L-tryptophan benzyl ester in 5 mL of THF containing 0.31 mL (2.2 mmol) of $Et_3N$, 0.178 g (1.1 mmol) of CDI was added. After 15 min 0.319 g (1.05 mmol) of 1-methanesulfonyl-spiroindoline-3,4'-piperidine hydrochloride and 0.16 mL (1.1 mmol) of $Et_3N$ were added and the mixture was stirred overnight. The reaction was partitioned between water and EtOAc and the layers were separated. The EtOAc layer was washed with brine, dried and concentrated. The residue was chromatographed on a flash column using 70% EtOAc-Hexane to isolate 0.58 g of the title compound.

$^1$H NMR ($CDCl_3$) δ1.5–1.75 (m, 4H), 2.87 (m, 2H), 2.87 (s, 3H), 3.3 (m, 2H), 3.74 (s, 2H), 3.78 (t, 2H), 4.91 (q, 1H), 5.03 (br s, 1H), 5.06 and 5.18 (ABq, 2H), 6.65 (d, 1H), 7–7.55 (m, 13H), 8.17 (br s, 1H).

Mass spectrum m/z=587.8 (M+1).

Step B: 2-(S)-((1-Methanesulfonyl-spiroindoline-3,4'-piperidino)-carbonyl-amino)-3-(3-indolyl)propionic acid A solution of 0.46 g (0.784 mmol) of benzyl 2-(S)-((1-methanesulfonyl-spiroindoline-3,4'-piperidino)-carbonyl-amino)-3-(3-indolyl)propionate in 10 mL of ethanol containing 46 mg of 10% Pd/C was hydrogenated on a Parr apparatus at 40 psi. After 8 h the reaction was ca. 50% complete. The catalyst was filtered, washed with EtOAc and the combined filtrate was concentrated. The residue was dissolved in 5 mL of EtOH, diluted with 5 mL of EtOAc and 10 drops of acetic acid (HOAc) were added. Fresh 10% Pd/C (50 mg) was added and the mixture was hydrogenated on a Parr apparatus for 3 h. The catalyst was filtered through a pad of celite, the pad was rinsed with EtOAc and the combined filtrate was concentrated to yield 0.39 g of the title compound which was used in the next step without purification.

$^1$H NMR (CDCl$_3$) δ1.35–1.7 (m, 4H), 2.6 (t, 2H), 2.84 (s, 3H), 3.33 (br s, 2H), 3.45–3.8 (m, 4H), 4.75 (m, 1H), 5.15 (s, 1H), 6.9–7.6 (m, 9H), 8.6 (br s, 1H).

Step C: N-Benzyl-2-(S)-((1-methanesulfonyl-spiroindoline-3,4'-piperidino)-carbonyl-amino)-3-(3-indolyl) propionamide (L-744,394)

A solution of 81 mg (0.163 mmol) of 2-(S)-((1-methanesulfonyl-spiroindoline-3,4'-piperidino)-carbonyl-amino)-3-(3-indolyl)propionic acid in 1 mL of CH$_2$Cl$_2$ was treated with 27 uL (0.245 mmol) of N-methylmorpholine, 26 mg (0.196 mmol) of hydroxybenzotriazol and 39 mg (0.196 mmol) of EDC. After 15 min 20 uL (0.179 mmol) of benzylamine was added and the solution was stirred for 2.5 h. The reaction was quenched by adding water, then extraced with CH$_2$Cl$_2$. The organic layer was washed with brine, dried and concentrated. The residue was purified by prep TLC using EtOAc as eluant to isolate 80 mg of the title product.

$^1$H NMR (CDCl$_3$) d 1.5–1.85 (m, 4H), 2.78 (q, 2H), 2.87 (s, 3H), 3.18 (dd, 1H), 3.35 (dd, 1H), 3.74 (s, 2H), 3.82 (m, 2H), 4.2–4.4 (m, 2H), 4.7 (m, 1H), 6.9–7.5 (m, 13H), 7.68 (d, 1H), 8.16 (br s, 1H).

Mass spectrum m/z=586.8 (M+1).

EXAMPLE 3

3,5-Bistrifluoromethylbenzyl 2-(S)-((spiro-1H-indene-1,4'-piperidino)-carbonyl-amino)-3-(3-indolyl)propionate The title compound was prepared the method of example 1 by substituting 3,5-bistrifluoromethylbenzyl alcohol for N-benzyl-N-methylamine in step A.

$^1$H NMR (CDCl$_3$) δ1.3 (m, 2H), 1.93 (m, 2H), 3.1 (m, 2H), 3.84 (br d, 1H), 3.96 (br d, 1H), 4.9 (q, 1H), 5.07 (d, 1H), 5.11 (s, 2H), 6.7–7.8 (14H), 8.18 (br s, 1H).

EXAMPLE 4

N-Benzyl-N-methyl-2-(S)-((spiroindane-1,4'-piperidino)-carbonyl-amino)-3-(3-indolyl) propionamide Hydrogenation of N-benzyl-N-methyl-2-(S)-((spiro-1H-indene-1,4'-piperidino)-carbonyl-amino)-3-(3-indolyl) propionamide (from example 1) in ethanol in a Parr apparatus with 10% Pd/C as a catalyst furnished the title compound.

$^1$H NMR (CDCl$_3$, ppm ranges are listed because amide rotomers were present) δ1.5 (m, 2H), 1.75 (m, 2H), 2.04 (m, 2H), 2.59 and 2.79 (2s, 3H), 2.85–3.3 (m, 4H), 3.8–4.6 (m, 4H), 5.27 (m, 1H), 5.46 and 5.54 (2d, 1H), 6.9–7.4 (m, 13H), 7.49 and 7.70 (2d, 1H), 8.15 and 8.25 (2br s, 1H).

Mass spectrum m/z=521.7 (M+1).

The following compounds (examples 5–13) were synthesized by the procedure of example 1 by substituting spiro-1H-indene-1,4'-piperidine with an appropriate amine in step C.

EXAMPLE 5

N-Benzyl-N-methyl-2-(S)-((1-methanesulfonyl-spiroindoline-3,4'-piperidino)-carbonyl-amino)-3-(3-indolyl)propionamide $^1$H NMR (CDCl$_3$, ppm ranges are listed because amide rotomers were present) δ1.5–1.9 (m, 4H), 2.6–3.3 (m, 10H), 3.8–4.6 (m, 6H), 5.26 (m, 1H), 5.49 and 5.59 (2m, 1H), 6.9–7.4 (m, 15H), 7.5 and 7.71 (2d, 1H), 8.13 and 8.23 (2br s, 1H).

EXAMPLE 6

N-Benzyl-N-methyl-2-(S)-((1-acetylspiroindoline-3,4'-piperidino)-carbonyl-amino)-3-(3-indolyl) propionamide Mass spectrum m/z=564 (M+1).

EXAMPLE 7

N-Benzyl-N-methyl-2-(S)-(4-phenylpiperidino)-carbonyl-amino)-3-(3-indolyl)propionamide $^1$H NMR (CDCl$_3$, ppm ranges are listed because amide rotomers were present) δ1.5–1.9 (m, 5H), 2.5–3.3 (m, 7H), 4.0–4.6 (m, 4H), 5.2 (br, 1H), 5.55 (br, 1H) 6.9–7.4 (m, 14H), 7.5 and 7.7 (2d, 1H), 8.05 and 8.13 (2br s, 1H).

Mass spectrum m/z=495 (M+1).

EXAMPLE 8

N-Benzyl-N-methyl-2-(S)-((4-benzylpiperidino)-carbonyl-amino)-3-(3-indolyl)propionamide $^1$H NMR (CDCl$_3$, ppm ranges are listed because amide rotomers were present) δ1–1.9 (m, 4H), 2.4–3.3 (m, 9H), 3.8–4.6 (m, 4H), 5.1–5.5 (m, 2H), 6.8–7.4 (m, 14H), 7.47 and 7.67 (2d, 1H), 8.05 and 8.2 (br, 1H).

Mass spectrum m/z=509 (M+1).

EXAMPLE 9

N-Benzyl-N-methyl-2-(S)-(((4-phenyl-4-acetylamino)piperidino)-carbonyl-amino)-3-(3-indolyl)propionamide Mass spectrum m/z=552 (M+1).

EXAMPLE 10

N-Benzyl-N-methyl-2-(S)-((4-benzylpiperazino)-carbonyl-amino)-3-(3-indolyl)propionamide $^1$H NMR (CDCl$_3$, ppm ranges are listed because amide rotomers were present) δ2.36 (m, 4H), 2.56 and 2.76 (2s, 3H), 3.1–3.6 (m, 8H), 4.05–4.55 (m, 2H), 5.29 (m, 1H), 5.45 and 5.53 (2br, 1H), 6.8–7.3 (m, 14H), 7.48 and 7.66 (2d, 1H), 8.25 (br, 1H).

Mass spectrum m/z=510.7 (M+1).

EXAMPLE 11

N-Benzyl-N-methyl-2-(S)-(4-(2-oxo-1,2,3,4-tetrahydroquinazolin-1-yl)piperidino)-carbonyl-amino)-3-(3-indolyl)propionamide Mass spectrum m/z=565 (M+1).

EXAMPLE 12

N-Benzyl-N-methyl-2-(S)-((4-(2-methoxyphenyl) piperazino)-carbonyl-amino)-3-(3-indolyl) propionamide Mass spectrum m/z=526 (M+1).

EXAMPLE 13

N-Benzyl-N-methyl-2-(S)-((4-(2-methylphenyl) piperazino)-carbonyl-amino)-3-(3-indolyl) propionamide Mass spectrum m/z=510 (M+1).

The following compounds (examples 14–30) were prepared by a procedure analogous to that described in example 2.

EXAMPLE 14

N-Phenyl-2-(S)-((spiroindane-1,4'-piperidino)-carbonyl-amino)-3-(3-indolyl)propionamide ¹H NMR (CDCl₃) δ1.42 (m, 2H), 1.5–1.8 (m, 2H), 1.95 (t, 2H), 2.87 (m, 4H), 3.2–3.45 (m, 2H), 3.72 (br d, 1H), 3.87 (br d, 1H), 4.88 (q, 1H), 5.4 (br s, 1H), 6.9–7.4 (m, 13H), 7.7 (d, 1H), 8.23 (br s, 1H), 8.8 (br s, 1H).

Mass spectrum m/z=493.6 (M+1).

EXAMPLE 15

N-Benzyl-2-(S)-((spiroindane-1,4'-piperidino)-carbonyl-amino)-3-(3-indolyl)propionamide ¹H NMR (CDCl₃) δ1.45 (m, 2H), 1.7 (m, 2H), 1.99 (t, 2H), 2.89 (m, 4H), 3.17 (dd, 1H), 3.37 (dd, 1H), 3.75 (br d, 1H), 3.86 (br d, 1H), 4.3 (m, 2H), 4.71 (q, 1H), 5.28 (d, 1H), 6.3 (br s, 1H), 6.9–7.4 (m, 13H), 7.71 (d, 1H), 8.1 (br s, 1H).

Mass spectrum m/z=507.8 (M+1).

EXAMPLE 16

N-(2-Methylbenzyl)-2-(S)-((spiroindane-1,4'-piperidino)-carbonyl-amino)-3-(3-indolyl)propionamide ¹H NMR (CDCl₃) δ1.4–1.8 (m, 4H), 1.98 (t, 2H), 2.12 (s, 3H), 2.89 (m, 4H), 3.17 (dd, 1H), 3.36 (dd, 1H), 3.75 (br d, 1H), 3.86 (br d, 1H), 4.28 (m, 2H), 4.71 (q, 1H), 5.31 (br, 1H), 6.25 (br s, 1H), 6.9–7.4 (m, 12H), 7.7 (d, 1H), 8.2 (br s, 1H).

Mass spectrum m/z=521.7 (M+1).

EXAMPLE 17

N-(3-Methylbenzyl)-2-(S)-((spiroindane-1,4'-piperidino)-carbonyl-amino)-3-(3-indolyl)propionamide ¹H NMR (CDCl₃) δ1.4–1.8 (m, 4H), 1.99 (t, 2H), 2.27 (s, 3H), 2.89 (m, 4H), 3.17 (dd, 1H), 3.36 (dd, 1H), 3.76 (br d, 1H), 3.87 (br d, 1H), 4.25 (m, 2H), 4.7 (q, 1H), 5.29 (br, 1H), 6.3 (br s, 1H), 6.8–7.4 (m, 12H), 7.71 (d, 1H), 8.2 (br s, 1H).

Mass spectrum m/z=521.8 (M+1).

EXAMPLE 18

N-(4-Methylbenzyl)-2-(S)-((spiroindane-1,4'-piperidino)-carbonyl-amino)-3-(3-indolyl)propionamide ¹H NMR (CDCl₃) δ1.4–1.8 (m, 4H), 1.97 (t, 2H), 2.28 (s, 3H), 2.88 (m, 4H), 3.18 (dd, 1H), 3.35 (dd, 1H), 3.74 (br d, 1H), 3.85 (br d, 1H), 4.26 (m, 2H), 4.71 (q, 1H), 5.32 (br, 1H), 6.4 (br s, 1H), 6.8–7.4 (m, 12H), 7.7 (d, 1H), 8.3 (br s, 1H).

Mass spectrum m/z=521.8 (M+1).

EXAMPLE 19

N-(2-Phenylethyl)-2-(S)-((spiroindane-1,4'-piperidino)-carbonyl-amino-3-(3-indolyl)propionamide ¹H NMR (CDCl₃) δ1.43 (m, 2H), 1.7 (m, 2H), 1.99 (t, 2H), 2.56 (m, 2H), 2.89 (m, 4H), 3.14 (dd, 1H), 3.38 (m, 3H), 3.73 (br d, 1H), 3.84 (br d, 1H), 4.62 (q, 1H), 5.22 (br s, 1H), 5.92 (br s, 1H), 6.9–7.4 (m, 13H), 7.7 (d, 1H), 8.24 (br s, 1H).

Mass spectrum m/z=521.7 (M+1).

EXAMPLE 20

N-Benzyl-N-ethyl-2-(S)-((spiroindane-1,4'-piperidino)-carbonyl-amino)-3-(3-indolyl)propionamide Mass spectrum m/z=535.8 (M+1).

EXAMPLE 21

N-(1(S)-Phenylethyl)-2(S)-((spiroindane-1,4'-piperidino)-carbonyl-amino)-3-(3-indolyl)propionamide Mass spectrum m/z=521.8 (M+1).

EXAMPLE 22

N-(1(R)-Phenylethyl)-2(S)-((spiroindane-1,4'-piperidino)-carbonyl-amino)-3-(3-indolyl)propionamide Mass spectrum m/z=521.8 (M+1).

EXAMPLE 23

N-(1(S)-Phenylpropyl)-N-methyl-2(S)-((spiroindane-1,4'-piperidino)-carbonyl-amino)-3-(3-indolyl)propionamide Mass spectrum m/z=535.8 (M+1).

EXAMPLE 24

N-(1(R)-Phenylpropyl)-N-methyl-2(S)-((spiroindane-1,4'-piperidino)-carbonyl-amino)-3-(3-indolyl)propionamide Mass spectrum m/z=535.8 (M+1).

EXAMPLE 25

N-(3-Methylphenyl)methyl-N-methyl-2-(S)-((1-methanesulfonyl-spiroindoline-3,4'-piperidino)-carbonyl-amino)-3-(3-indolyl)propionamide ¹H NMR (CDCl₃, ppm ranges are listed because amide rotomers were present) δ1.5–1.9 (m, 4H), 2.1–3.3 (m, 13H), 3.7–4.6 (m, 6H), 5.22 (m, 1H), 5.5 and 5.6 (2br, 1H), 6.8–7.4 (m, 12H), 7.69 (d, 1H), 8.2 (br, 1H).

Mass spectrum m/z=614 (M+1).

EXAMPLE 26

N-(3-Trifluoromethylphenyl)methyl-N-methyl-2-(S)-((1-methanesulfonyl-spiroindoline-3,4'-piperidino)-carbonyl-amino)-3-(3-indolyl)propionamide (L-746, 895)

Mass spectrum m/z=668.2 (M+1).

EXAMPLE 27

N-(3,5-Dichlorophenyl)methyl-N-methyl-2-(S)-((1-methanesulfonyl-spiroindoline-3,4'-piperidino)-carbonyl-amino)-3-(3-indolyl)propionamide ¹H NMR (CDCl₃, ppm ranges are listed because amide rotomers were present) δ1.6–1.9 (m, 4H), 2.5–3.3 (m, 10H), 3.8–4.6 (m, 6H), 5.1–5.5 (m, 2H), 6.9–7.4 (m, 15H), 7.5 and 7.7 (2d, 1H), 8.1(1br, 1H).

EXAMPLE 28

N-(3,5-Dimethylphenyl)methyl-N-methyl-2-(S)-((1-methanesulfonyl-spiroindoline-3,4'-piperidino)-carbonyl-amino)-3-(3-indolyl)propionamide Mass spectrum m/z=628.4 (M+1).

EXAMPLE 29

N-((3-Chloro-5-methyl)phenyl)methyl-N-methyl-2-(S)-((1-methanesulfonyl-Spiroindoline-3,4'-piperidino)-carbonyl-amino)-3-(3-indolyl)propionamide Mass spectrum m/z =648.4 (M+1).

EXAMPLE 30

N-(1(S)-phenyl)ethyl-N-methyl-2-(S)-((1-methanesulfonyl-spiroindoline-3,4'-piperidino)-carbonyl-amino)-3-(3-indolyl)propionamide Mass spectrum m/z=616 (M+1).

The compounds of examples 31–37 were prepared by the method of example 1 starting with the appropriate boc-amino acid.

EXAMPLE 31

N-Benzyl-N-methyl-2-(R)-((spiro-1H-indene-1,4'-piperidino)-carbonyl-amino)-3-(3-indolyl)propionamide Mass spectrum m/z=519 (M+1).

EXAMPLE 32

N-Benzyl-N-methyl-2-(R)-((1-methanesulfonyl-spiroindoline-3,4'-piperidino)-carbonyl-amino)-3-(3-indolyl)propionamide Mass spectrum m/z=600 (M+1).

EXAMPLE 33

N-Benzyl-N-methyl-2-(R)-(4-phenylpiperidino)-carbonyl-amino)-3-(3-indolyl)propionamide Mass spectrum m/z=495 (M+1).

EXAMPLE 34

N-Benzyl-N-methyl-2-(S)-((1-methanesulfonyl-spiroindoline-3,4'-piperidino)-carbonyl-amino)-4-phenylbutyramide $^1$H NMR (CDCl$_3$, ppm ranges are listed because amide rotomers were present) d 1.6–2.0 (m, 4H), 2.6–3.0 (m, 10H), 3.8–4.05 (m, 4H), 4.3–5.0 (m, 3H), 5.5 and 5.57 (2br s, 1H), 7.0–7.4 (m, 14H).

EXAMPLE 35

N-Benzyl-N-methyl-2-(S)-((1-methanesulfonyl-spiroindoline-1,4'-piperidino)-carbonyl-amino)-3-benzyloxypropionamide Mass spectrum m/z=591 (M+1).

EXAMPLE 36

N-Benzyl-N-methyl-2-(S)-((spiroindine-1,4'-piperidino)-carbonyl-amino)-3-phenylpropionamide $^1$H NMR (CDCl$_3$, ppm ranges are listed because amide rotomers were present) δ1.34 (m, 2H), 2.0 (m, 2H), 2.66 and 2.85 (2s, 3H), 2.95–3.3 (m, 4H), 3.9–4.7 (m, 4H), 5.15 (m, 1H), 5.36 and 5.47 (2d, 1H), 6.7–7.35 (m, 16H).

EXAMPLE 37

N-Benzyl-N-methyl-2-(S)-((spiroindine-1,4'-piperidino)-carbonyl-amino)-2-phenylacetamide $^1$H NMR (CDCl$_3$, ppm ranges are listed because amide rotomers were present) δ1.34 (m, 2H), 2.0 (m, 2H), 2.82 and 2.87 (2s, 3H), 3.16 (m, 2H), 4.0–4.75 (m, 4H), 5.87 and 5.92 (2d, 1H), 6.23 (m, 1H), 6.7–7.5 (m, 16H).

TABLE 1

| Example No | hNK$_1$(IC$_{50}$ nM) | hNK$_2$(IC$_{50}$ nM) |
| --- | --- | --- |
| 1 | 40 | 10 |
| 2 | 70 | 40 |
| 3 | 1 | >1000 |
| 4 | 50 | 8 |
| 5 | 20 | 12 |
| 6 | 15 | 30 |
| 7 | 60 | 50 |
| 8 | 90 | 25 |
| 9 | 60 | >100 |
| 10 | 60 | 100 |
| 11 | 100 | 60 |
| 12 | 20 | 25 |
| 13 | 30 | 15 |
| 14 | >1000 | 650 |
| 15 | 100 | 35 |
| 16 | 100 | 15 |
| 17 | 60 | 65 |
| 18 | 100 | 200 |
| 19 | 200 | 56 |
| 20 | 120 | 25 |
| 21 | 80 | 16 |
| 22 | 1000 | 28 |
| 23 | 650 | 30 |
| 24 | 1000 | 50 |
| 25 | 8 | 85 |
| 26 | 7.5 | 127 |
| 27 | 1 | 180 |
| 28 | 3 | >300 |
| 29 | 2 | 500 |
| 30 | 10 | 70 |
| 31 | 600 | 130 |
| 32 | 200 | 180 |
| 33 | 750 | 250 |
| 34 | 400 | 60 |
| 35 | 300 | 60 |
| 36 | 300 | 200 |
| 37 | 575 | 200 |

What is claimed is:

1. A compound of formula I

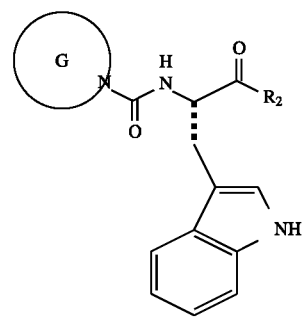

or a pharmaceutically acceptable salt thereof, wherein

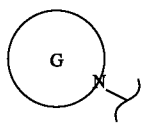

is selected from the group consisting of

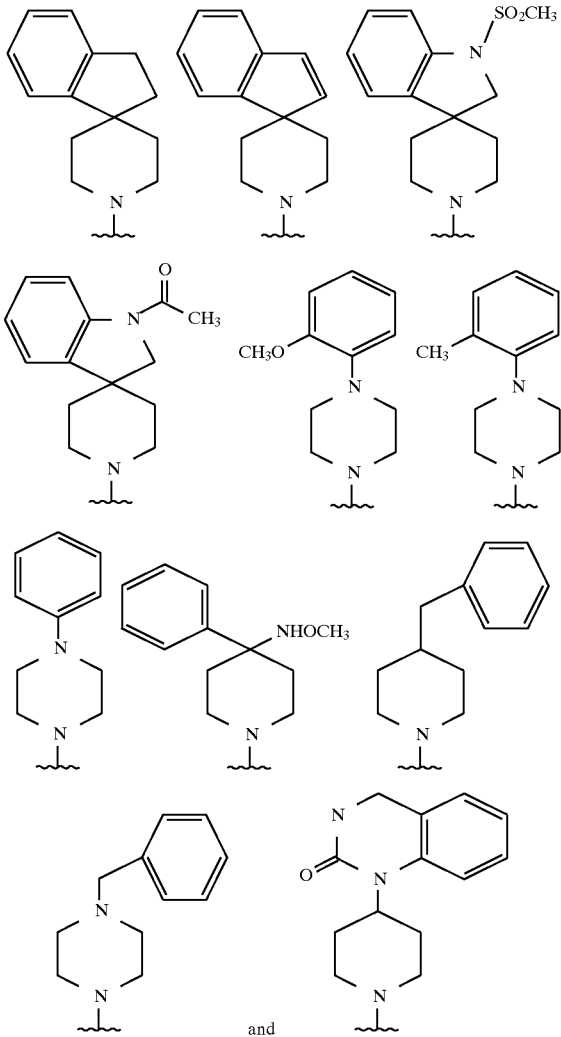

and

R₂ is selected from
(a) —OCH₂phenyl, wherein the phenyl is optionally mono di or trisubstituted phenyl wherein the substitutents are independently halo, methyl or CF₃; and
(b) —N(R₃)C₁₋₄alkylphenyl, wherein the C₁₋₄alkyl may be linear or branched, the phenyl is optionally mono di or trisubstituted and wherein the substitutents are independently halo, methyl, methoxy or CF₃ and R₃ is H, methyl or ethyl.

2. A compound according to claim 1 wherein R₂ is selected from
(a) —OCH₂phenyl, wherein the phenyl is optionally mono di or trisubstituted phenyl wherein the substitutents are independently halo, methyl, methoxy or CF₃;
(b) —NHCH₂phenyl, wherein the phenyl is optionally mono di or trisubstituted phenyl wherein the substitutents are independently halo, methyl, methoxy or CF₃;
(c) —N(CH₃)CH₂phenyl, wherein the phenyl is optionally mono di or trisubstituted phenyl wherein the substitutents are independently halo, methyl, methoxy or CF₃;
(d) —N(CH₃)CH(CH₃)phenyl, wherein the phenyl is optionally mono di or trisubstituted phenyl wherein the substitutents are independently halo, methyl, methoxy or CF₃; and
(f) —N(CH₃)CH(CH₂CH₃)phenyl, wherein the phenyl is optionally mono di or trisubstituted phenyl wherein the substitutents are independently halo, methyl, methoxy or CF₃.

3. A compound according to claim 2 wherein

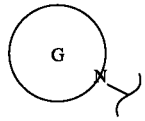

is selected from the group consisting of

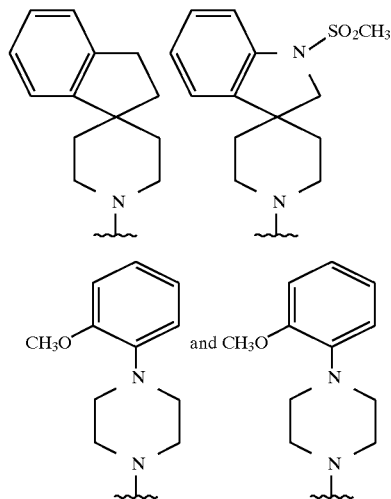

4. A compound according to claim 3 wherein R₂ is selected from
(a) —OCH₂phenyl, wherein the phenyl is optionally mono di or trisubstituted phenyl wherein the substitutents are independently chloro, methyl or CF₃;
(b) —NHCH₂phenyl, wherein the phenyl is optionally mono di or trisubstituted phenyl wherein the substitutents are independently chloro, methyl or CF₃;
(c) —N(CH₃)CH₂phenyl, wherein the phenyl is optionally mono di or trisubstituted phenyl wherein the substitutents are independently chloro, methyl or CF₃; and
(d) —N(CH₃)CH(CH₃)phenyl, wherein the phenyl is optionally mono di or trisubstituted phenyl wherein the substitutents are independently chloro, methyl or CF₃.

5. A compound according to claim 4 wherein R₂ is selected from
(a) —OCH₂phenyl, wherein the phenyl is optionally mono di or trisubstituted phenyl wherein the substitutents are independently chloro, methyl or CF₃;
(b) —NHCH₂phenyl, wherein the phenyl is optionally mono di or trisubstituted phenyl wherein the substitutents are independently chloro, methyl or CF₃; and (c) —N(CH₃)CH₂phenyl, wherein the phenyl is optionally mono di or trisubstituted phenyl wherein the substitutents are independently chloro, methyl or CF₃.

6. A compound according to claim 1 selected from
(a) N-Benzyl-N-methyl-2-(S)-((spiro-1H-indene-1,4'-piperidino)-carbonyl-amino)-3-(3-indolyl)propionamide,
(b) N-Benzyl-2-(S)-((1-methanesulfonyl-spiroindoline-3,4'-piperidino)-carbonyl-amino)-3-(3-indolyl) propionamide,
(c) 3,5-Bistrifluoromethylbenzyl 2-(S)-((spiro-1H-indene-1,4'-piperidino)-carbonyl-amino)-3-(3-indolyl)propionate,
(d) N-Benzyl-N-methyl-2-(S)-((spiroindane-1,4'-piperidino)-carbonyl-amino)-3-(3-indolyl)propionamide,
(e) N-Benzyl-N-methyl-2-(S)-((1-methanesulfonyl-spiroindoline-3,4'-piperidino)-carbonyl-amino)-3-(3-indolyl)propionamide,
(f) N-Benzyl-N-methyl-2-(S)-((1-acetylspiroindoline-3,4'-piperidino)-carbonyl-amino)-3-(3-indolyl)propionamide,
(g) N-Benzyl-N-methyl-2-(S)-(4-phenylpiperidino)-carbonyl-amino)-3-(3-indolyl)propionamide,
(h) N-Benzyl-N-methyl-2-(S)-((4-benzylpiperidino)-carbonyl-amino)-3-(3-indolyl)propionamide,
(i) N-Benzyl-N-methyl-2-(S)-(((4-phenyl-4-acetylamino) piperidino)-carbonyl-amino)-3-(3-indolyl)propionamide,
(j) N-Benzyl-N-methyl-2-(S)-((4-benzylpiperazino)-carbonyl-amino)-3-(3-indolyl)propionamide,
(k) N-Benzyl-N-methyl-2-(S)-(4-(2-oxo-1,2,3,4-tetrahydroquinazolin-1-yl)piperidino)-carbonyl-amino)-3-(3-indolyl)propionamide,
(l) N- Benzyl-N-methyl-2-(S)-((4-(2-methoxyphenyl) piperazino)-carbonyl-amino)-3-(3-indolyl)propionamide,
(m) N-Benzyl-N-methyl-2-(S)-((4-(2-methylphenyl) piperazino)-carbonyl-amino)-3-(3-indolyl)propionamide,
(n) N-Phenyl-2-(S)-((spiroindane-1,4'-piperidino)-carbonyl-amino)-3-(3-indolyl)propionamide,
(o) N-Benzyl-2-(S)-((spiroindane-1,4'-piperidino)-carbonyl-amino)- 3-(3-indolyl)propionamide,
(p) N-(2-Methylbenzyl)-2-(S)-((spiroindane-1,4'-piperidino)-carbonyl-amino)-3-(3-indolyl)propionamide,
(o) N-(3-Methylbenzyl)-2-(S)-((spiroindane-1,4'-piperidino)-carbonyl-amino)-3-(3-indolyl)propionamide,
(p) N-(4-Methylbenzyl)-2-(S)-((spiroindane-1,4'-piperidino)-carbonyl-amino)-3-(3-indolyl)propionamide,
(q) N-(2-Phenylethyl)-2-(S)-((spiroindane-1,4'-piperidino)-carbonyl-amino)-3-(3-indolyl)propionamide,
(r) N-Benzyl-N-ethyl-2-(S)-((spiroindane-1,4'-piperidino)-carbonyl-amino)-3-(3-indolyl)propionamide,
(s) N-(1(S)-Phenylethyl)-2(S)-((spiroindane-1,4'-piperidino)-carbonyl-amino)-3-(3-indolyl)propionamide,
(t) N-(1(R)-Phenylethyl)-2(S)-((spiroindane-1,4'-piperidino)-carbonyl-amino)-3-(3-indolyl)propionamide,
(u) N-(1(S)-Phenylpropyl)-N-methyl-2(S)-((spiroindane-1,4'-piperidino)-carbonyl-amino)-3-(3-indolyl) propionamide,
(v) N-(1(R)-Phenylpropyl)-N-methyl-2(S)-((spiroindane-1,4'-piperidino)-carbonyl-amino)-3-(3-indolyl) propionamide,
(w) N-(3-Methylphenyl)methyl-N-methyl-2-(S)-((1-methanesulfonyl-spiroindoline-3,4'-piperidino)-carbonyl-amino)-3-(3-indolyl)propionamide,
(x) N-(3-Trifluoromethylphenyl)methyl-N-methyl-2-(S)-((1-methanesulfonyl-spiroindoline-3,4'-piperidino)-carbonyl-amino)-3-(3-indolyl)propionamide,
(y) N-(3,5-Dichlorophenyl)methyl-N-methyl-2-(S)-((1-methanesulfonyl-spiroindoline-3,4'-piperidino)-carbonyl-amino)-3-(3-indolyl)propionamide,
(ab) N-(3,5-Dimethylphenyl)methyl-N-methyl-2-(S)-((1-methanesulfonyl-spiroindoline-3,4'-piperidino)-carbonyl-amino)-3-(3-indolyl)propionamide,
(ac) N-((3-Chloro-5-methyl)phenyl)methyl-N-methyl-2-(S)-((1-methanesulfonyl-spiroindoline-3,4'-piperidino)-carbonyl-amino)-3-(3-indolyl)propionamide,
(ad) N-(1(S)-phenyl)ethyl-N-methyl-2-(S)-((1-methanesulfonyl-spiroindoline-3,4'-piperidino)-carbonyl-amino)-3-(3-indolyl)propionamide,
(ae) N-Benzyl-N-methyl-2-(R)-((spiro-1H-indene-1,4'-piperidino)-carbonyl-amino)-3-(3-indolyl)propionamide
(af) N-Benzyl-N-methyl-2-(R)-((1-methanesulfonyl-spiroindoline-3,4'-piperidino)-carbonyl-amino)-3-(3-indolyl)propionamide,
(ag) N-Benzyl-N-methyl-2-(R)-(4-phenylpiperidino)-carbonyl-amino)-3-(3-indolyl)propionamide,
(ah) N-Benzyl-N-methyl-2-(S)-((1-methanesulfonyl-spiroindoline-3,4'-piperidino)-carbonyl-amino)-4-phenylbutyramide,
(ai) N-Benzyl-N-methyl-2-(S)-((1-methanesulfonyl-spiroindoline-1,4'-piperidino)-carbonyl-amino)-3-benzyloxypropionamide,
(aj) N-Benzyl-N-methyl-2-(S)-((spiroindoline-1,4'-piperidino)-carbonyl-amino)-3-phenylpropionamide, and
(ak) N-Benzyl-N-methyl-2-(S)-((spiroindoline-1,4'-piperidino)-carbonyl-amino)-2-phenylacetamide.

7. A method of treating or preventing asthma in a patient in need thereof which comprises the administration to the patient of a non-toxic therapeutically effective amount of the compound of claim 1.

8. A pharmaceutical composition comprising a compound according to claim 1 in combination with a pharmaceutically acceptable carrier.

* * * * *